United States Patent
Webb et al.

(10) Patent No.: US 9,943,403 B2
(45) Date of Patent: Apr. 17, 2018

(54) FRACTURABLE MASK FOR TREATING PRESBYOPIA

(71) Applicant: AcuFocus, Inc., Irvine, CA (US)

(72) Inventors: R. Kyle Webb, Carlsbad, CA (US); Daniel David Siems, Aliso Viejo, CA (US)

(73) Assignee: AcuFocus, Inc., Irvine, CA (US)

(*) Notice: Subject to any disclaimer, the term of this patent is extended or adjusted under 35 U.S.C. 154(b) by 0 days.

(21) Appl. No.: 14/944,104

(22) Filed: Nov. 17, 2015

(65) Prior Publication Data

US 2016/0135947 A1 May 19, 2016

Related U.S. Application Data (60) Provisional application No. 62/082,007, filed on Nov. 19, 2014.

(51) Int. Cl.
*B29D 11/00* (2006.01)
*A61F 2/16* (2006.01)
(Continued)

(52) U.S. Cl.
CPC ............... *A61F 2/16* (2013.01); *A61F 2/15* (2015.04); *B29D 11/023* (2013.01);
(Continued)

(58) Field of Classification Search
CPC ...... A61F 2/14; A61F 2/16; A61F 2002/1696; A61F 2/15; B29D 11/023
See application file for complete search history.

(56) References Cited

U.S. PATENT DOCUMENTS

| | | |
|---|---|---|
| 2,350,421 A | 6/1944 | Schoder et al. |
| 2,470,927 A | 5/1949 | Hale, Jr. |

(Continued)

FOREIGN PATENT DOCUMENTS

| | | |
|---|---|---|
| AU | 2004201751 | 5/2004 |
| CN | 1875895 | 12/2006 |

(Continued)

OTHER PUBLICATIONS

Internet Archive Wayback Machine; Aniridia Implants; downloaded from https://web.archive.org/web/20110824062840/http://www.morcher.com/nc/produkte/aniridiaimplants.html (Archived Aug. 24, 2011; printed on Feb. 5, 2015).

(Continued)

*Primary Examiner* — Mathieu Vargot
(74) *Attorney, Agent, or Firm* — Knobbe Martens Olson & Bear LLP (57) ABSTRACT

A fracturable mask for treating presbyopia is disclosed. The fracturable mask can include an aperture for improving depth of focus. The fracturable mask can be embedded in an intraocular lens. The intraocular lens can include a lens body and the fracturable mask. The fracturable mask can be configured to fracture along a plurality of fracture pathways when the intraocular lens is manipulated. For example, fractures can be created in the mask during the process of injecting the intraocular lens through a cartridge tip into a patient's eye. The fractures can allow the resilient lens body to restore the fractured mask to its original, pre-injection optical performance specifications.

16 Claims, 8 Drawing Sheets

(51) Int. Cl.
*B29D 11/02* (2006.01)
*A61F 2/14* (2006.01)
(52) U.S. Cl.
CPC . *A61F 2002/1696* (2015.04); *A61F 2240/001* (2013.01); *A61F 2250/0018* (2013.01)

(56) References Cited

U.S. PATENT DOCUMENTS

| | | |
|---|---|---|
| 3,034,403 A | 5/1962 | Neefe |
| 3,270,099 A | 8/1966 | Camp |
| 3,458,870 A | 8/1969 | Stone |
| 3,578,850 A | 5/1971 | Grant |
| 3,776,230 A | 12/1973 | Neefe |
| 3,794,414 A | 2/1974 | Wesley |
| 3,877,502 A | 4/1975 | Hunckler |
| 3,996,627 A | 12/1976 | Deeg et al. |
| 4,010,496 A | 3/1977 | Neefe |
| 4,104,338 A | 8/1978 | Guerrieri |
| 4,116,439 A | 9/1978 | Chavarria et al. |
| 4,210,391 A | 7/1980 | Cohen |
| 4,298,996 A | 11/1981 | Barnet |
| 4,340,283 A | 7/1982 | Cohen |
| 4,402,579 A | 9/1983 | Poler |
| 4,423,728 A | 1/1984 | Lieberman |
| 4,435,050 A | 3/1984 | Poler |
| 4,450,593 A | 5/1984 | Poler |
| 4,505,855 A | 3/1985 | Bruns et al. |
| 4,563,565 A | 1/1986 | Kampfer et al. |
| 4,575,373 A | 3/1986 | Johnson |
| 4,607,617 A | 8/1986 | Choyce |
| 4,624,669 A | 11/1986 | Grendahl |
| 4,639,105 A | 1/1987 | Neefe |
| 4,646,720 A | 3/1987 | Peyman et al. |
| 4,655,774 A | 4/1987 | Choyce |
| 4,665,913 A | 5/1987 | Esperance, Jr. |
| 4,669,466 A | 6/1987 | L'Esperance |
| 4,669,834 A | 6/1987 | Richter |
| 4,676,790 A | 6/1987 | Kern |
| 4,676,791 A | 6/1987 | LeMaster et al. |
| 4,678,422 A | 7/1987 | York |
| 4,701,038 A | 10/1987 | Neefe |
| 4,715,858 A | 12/1987 | Lindstrom |
| 4,767,647 A | 8/1988 | Bree |
| 4,795,462 A | 1/1989 | Grendahl |
| 4,798,608 A | 1/1989 | Grendahl |
| 4,799,784 A | 1/1989 | Safir |
| 4,799,931 A | 1/1989 | Lindstrom |
| 4,807,623 A | 2/1989 | Lindstrom |
| 4,813,955 A | 3/1989 | Achatz et al. |
| 4,817,789 A | 4/1989 | Paul |
| 4,842,599 A | 6/1989 | Bronstein |
| 4,851,003 A | 7/1989 | Lindstrom |
| 4,863,466 A | 9/1989 | Schlegel |
| 4,881,860 A | 11/1989 | Kanazawa |
| 4,903,695 A | 2/1990 | Warner et al. |
| 4,907,586 A | 3/1990 | Bille et al. |
| 4,928,815 A | 5/1990 | Paul |
| 4,955,904 A | 9/1990 | Atebara et al. |
| 4,976,732 A | 12/1990 | Vorosmarthy |
| 4,994,080 A | 2/1991 | Shepard |
| 5,013,319 A | 5/1991 | Davis |
| 5,030,230 A | 7/1991 | White |
| 5,041,133 A | 8/1991 | Sayano et al. |
| 5,055,602 A | 10/1991 | Melpolder |
| 5,087,015 A | 2/1992 | Galley |
| 5,090,955 A | 2/1992 | Simon |
| 5,094,521 A | 3/1992 | Jolson et al. |
| 5,098,443 A | 3/1992 | Parel et al. |
| 5,112,328 A | 5/1992 | Taboada et al. |
| 5,120,120 A | 6/1992 | Cohen |
| 5,120,121 A | 6/1992 | Rawlings et al. |
| 5,137,441 A | 8/1992 | Fogarty |
| 5,147,395 A | 9/1992 | Willis |
| 5,171,318 A | 12/1992 | Gibson et al. |
| 5,185,107 A | 2/1993 | Blake |
| 5,188,494 A | 2/1993 | Hatin |
| 5,192,316 A | 3/1993 | Ting |
| 5,196,026 A | 3/1993 | Barrett et al. |
| 5,213,749 A | 5/1993 | Huss et al. |
| 5,260,727 A | 11/1993 | Oksman et al. |
| 5,266,241 A | 11/1993 | Parekh |
| 5,269,795 A | 12/1993 | Arnott |
| 5,269,812 A | 12/1993 | White |
| 5,274,404 A | 12/1993 | Michael |
| 5,288,436 A | 2/1994 | Liu et al. |
| 5,292,514 A | 3/1994 | Capecchi et al. |
| 5,300,116 A | 4/1994 | Chirila et al. |
| 5,312,330 A | 5/1994 | Klopotek |
| 5,314,439 A | 5/1994 | Sugita |
| 5,314,961 A | 5/1994 | Anton et al. |
| 5,332,802 A | 7/1994 | Kelman et al. |
| 5,336,261 A | 8/1994 | Barrett et al. |
| 5,354,331 A | 10/1994 | Schachar et al. |
| 5,358,520 A | 10/1994 | Patel |
| 5,372,580 A | 12/1994 | Simon et al. |
| 5,391,201 A | 2/1995 | Barrett et al. |
| 5,441,511 A | 8/1995 | Hanna |
| 5,474,548 A | 12/1995 | Knopp et al. |
| 5,507,740 A | 4/1996 | O'Donnell, Jr. |
| 5,547,468 A | 4/1996 | Simon et al. |
| D375,245 S | 11/1996 | Irving |
| 5,578,080 A | 11/1996 | McDonald |
| 5,603,774 A | 2/1997 | LeBoeuf et al. |
| 5,607,437 A | 3/1997 | Simon et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,647,865 A | 7/1997 | Swinger |
| 5,653,752 A | 8/1997 | Silvestrini et al. |
| 5,662,706 A | 9/1997 | Legerton et al. |
| 5,693,268 A | 12/1997 | Widman et al. |
| 5,697,923 A | 12/1997 | Poler |
| 5,702,440 A | 12/1997 | Portney |
| 5,708,049 A | 1/1998 | Katagiri et al. |
| 5,713,957 A | 2/1998 | Steele et al. |
| 5,722,971 A | 3/1998 | Peyman |
| 5,725,575 A | 3/1998 | O'Donnell, Jr. |
| 5,746,558 A | 5/1998 | Nygren et al. |
| 5,752,967 A | 5/1998 | Kritzinger et al. |
| 5,769,889 A | 6/1998 | Kelman |
| 5,774,202 A | 6/1998 | Abraham et al. |
| 5,824,086 A | 10/1998 | Silvestrini |
| 5,837,156 A | 11/1998 | Cumming |
| 5,843,105 A | 12/1998 | Mathis et al. |
| 5,864,128 A | 1/1999 | Plesko |
| 5,870,167 A | 2/1999 | Knopp et al. |
| 5,895,610 A | 4/1999 | Chang et al. |
| 5,905,561 A | 5/1999 | Lee et al. |
| 5,910,537 A | 6/1999 | Feingold et al. |
| 5,913,898 A | 6/1999 | Feingold et al. |
| 5,919,185 A | 7/1999 | Peyman |
| 5,925,294 A | 7/1999 | Shibuya |
| 5,964,748 A | 10/1999 | Peyman |
| 5,964,776 A | 10/1999 | Peyman |
| 5,965,330 A | 10/1999 | Evans et al. |
| 5,980,040 A | 11/1999 | Xu et al. |
| 6,017,121 A | 1/2000 | Chateau et al. |
| 6,063,073 A | 5/2000 | Peyman |
| 6,090,141 A | 7/2000 | Lindstrom |
| 6,102,946 A | 8/2000 | Nigam |
| 6,106,553 A | 8/2000 | Feingold et al. |
| 6,110,166 A | 8/2000 | Juhasz et al. |
| 6,138,307 A | 10/2000 | McDonald |
| 6,152,959 A | 11/2000 | Portney |
| 6,164,777 A | 12/2000 | Li et al. |
| 6,178,593 B1 | 1/2001 | Carlson |
| 6,197,019 B1 | 3/2001 | Peyman |
| 6,201,036 B1 | 3/2001 | Fedorov et al. |
| 6,203,538 B1 | 3/2001 | Peyman |
| 6,210,401 B1 | 4/2001 | Lai |
| 6,217,571 B1 | 4/2001 | Peyman |
| 6,217,596 B1 | 4/2001 | Farah |
| 6,221,067 B1 | 4/2001 | Peyman |

(56) References Cited

U.S. PATENT DOCUMENTS

| | | |
|---|---|---|
| 6,228,113 B1 | 5/2001 | Kaufman |
| 6,228,114 B1 | 5/2001 | Lee |
| 6,228,115 B1 | 5/2001 | Hoffmann et al. |
| 6,171,336 B1 | 6/2001 | Sawusch |
| 6,264,648 B1 | 7/2001 | Peyman |
| 6,277,146 B1 | 8/2001 | Peyman et al. |
| 6,280,470 B1 | 8/2001 | Peyman |
| 6,280,471 B1 | 8/2001 | Peyman et al. |
| 6,302,877 B1 | 10/2001 | Ruiz |
| 6,304,390 B1 | 10/2001 | Takanashi |
| 6,308,590 B1 | 10/2001 | Berto |
| 6,335,190 B1 | 1/2002 | Zhou et al. |
| 6,361,560 B1 | 3/2002 | Nigam |
| 6,376,153 B2 | 4/2002 | Uchikawa et al. |
| 6,387,379 B1 | 5/2002 | Goldberg et al. |
| 6,391,230 B1 | 5/2002 | Sarbadhikari |
| 6,416,179 B1 | 7/2002 | Lieberman et al. |
| 6,423,093 B1 | 7/2002 | Hicks et al. |
| 6,432,246 B1 | 8/2002 | Blake |
| 6,436,092 B1 | 8/2002 | Peyman |
| 6,458,141 B1 | 10/2002 | Peyman |
| 6,461,384 B1 | 10/2002 | Hoffmann et al. |
| 6,491,637 B2 | 12/2002 | Foster et al. |
| 6,497,700 B1 | 12/2002 | LaHaye |
| 6,515,006 B2 | 2/2003 | Horn |
| 6,551,307 B2 | 4/2003 | Peyman |
| 6,554,424 B1 | 4/2003 | Miller et al. |
| 6,554,860 B2 | 4/2003 | Hoffmann et al. |
| 6,555,103 B2 | 4/2003 | Leukel et al. |
| 6,575,573 B2 | 6/2003 | Lai et al. |
| 6,581,993 B2 | 6/2003 | Nigam |
| 6,588,902 B2 | 7/2003 | Isogai |
| 6,589,280 B1 | 7/2003 | Koziol |
| 6,607,527 B1 | 8/2003 | Ruiz et al. |
| 6,613,088 B1 | 9/2003 | Babizhayev |
| 6,638,304 B2 | 10/2003 | Azar |
| 6,648,741 B2 | 11/2003 | Schneider |
| 6,649,722 B2 | 11/2003 | Rosenzweig et al. |
| 6,655,804 B2 | 12/2003 | Streibig |
| 6,692,126 B1 | 2/2004 | Xie et al. |
| 6,702,807 B2 | 3/2004 | Peyman |
| 6,726,322 B2 | 4/2004 | Andino et al. |
| 6,740,116 B2 | 5/2004 | Morcher |
| 6,755,858 B1 | 6/2004 | White |
| 6,786,926 B2 | 9/2004 | Peyman |
| 6,811,256 B1 | 11/2004 | Becherer et al. |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,989,008 B2 | 1/2006 | Peyman |
| 7,001,374 B2 | 2/2006 | Peyman |
| 7,008,447 B2 | 3/2006 | Koziol |
| 7,025,455 B2 | 4/2006 | Roffman |
| 7,061,693 B2 | 6/2006 | Zalevsky |
| 7,099,057 B2 | 8/2006 | Parker et al. |
| 7,276,080 B2 | 10/2007 | Murakami et al. |
| 7,287,852 B2 | 10/2007 | Fiala |
| 7,364,674 B1 | 4/2008 | Hoover |
| 7,399,811 B2 | 7/2008 | Mentak et al. |
| 7,404,637 B2 | 7/2008 | Miller et al. |
| 7,404,638 B2 | 7/2008 | Miller et al. |
| 7,446,157 B2 | 11/2008 | Mentak et al. |
| 7,455,404 B2 | 11/2008 | Bandhauer et al. |
| 7,455,691 B2 | 11/2008 | Feingold et al. |
| 7,477,452 B2 | 1/2009 | Tsuruma |
| 7,491,350 B2 | 2/2009 | Silvestrini |
| 7,497,866 B2 | 3/2009 | Perez |
| 7,628,810 B2 | 12/2009 | Christie et al. |
| 7,641,337 B2 | 1/2010 | Altmann |
| 7,645,299 B2 | 1/2010 | Koziol |
| 7,745,555 B2 | 6/2010 | Mentak et al. |
| 7,842,367 B2 | 11/2010 | Mentak |
| 7,976,577 B2 | 7/2011 | Silvestrini |
| D645,337 S | 9/2011 | Hsu et al. |
| 8,043,371 B2 | 10/2011 | Paul et al. |
| 8,048,972 B2 | 11/2011 | Mentak et al. |
| 8,079,706 B2 | 12/2011 | Silvestrini et al. |
| D656,526 S | 3/2012 | Christie et al. |
| 8,241,354 B2 | 8/2012 | Hong et al. |
| 8,287,592 B2 | 10/2012 | Silvestrini |
| 8,343,215 B2 | 1/2013 | Miller et al. |
| D681,086 S | 4/2013 | Christie et al. |
| 8,420,753 B2 | 4/2013 | Mentak et al. |
| 8,460,374 B2 | 6/2013 | Christie et al. |
| 8,604,098 B2 | 12/2013 | Boydston et al. |
| 8,740,978 B2 | 6/2014 | Weeber et al. |
| 8,752,958 B2 | 6/2014 | Miller et al. |
| 8,858,624 B2 | 10/2014 | Christie et al. |
| 8,864,824 B2 | 10/2014 | Silvestrini et al. |
| 9,005,281 B2 | 4/2015 | Christie et al. |
| 9,138,142 B2 | 9/2015 | Christie et al. |
| 9,204,962 B2 | 12/2015 | Silvestrini |
| 9,427,311 B2 | 8/2016 | Christie et al. |
| 9,427,922 B2 | 8/2016 | Reboul et al. |
| 9,492,272 B2 | 11/2016 | Christie et al. |
| 9,545,303 B2 | 1/2017 | Vilupuru et al. |
| 9,573,328 B2 | 2/2017 | Reboul et al. |
| 9,603,704 B2 | 3/2017 | Silvestrini |
| 2012/0238091 A | 5/1994 | Hsieh et al. |
| 2001/0027314 A1 | 10/2001 | Peyman |
| 2001/0034516 A1 | 10/2001 | Peyman |
| 2001/0050750 A1 | 12/2001 | Breger |
| 2002/0010510 A1 | 1/2002 | Silverstrini |
| 2002/0082288 A1 | 6/2002 | Horn |
| 2002/0120329 A1 | 8/2002 | Lang et al. |
| 2002/0167640 A1 | 11/2002 | Francis et al. |
| 2002/0196409 A1 | 12/2002 | Jani |
| 2003/0014042 A1 | 1/2003 | Juhasz et al. |
| 2003/0105521 A1 | 6/2003 | Perez |
| 2003/0135272 A1 | 7/2003 | Brady et al. |
| 2003/0149480 A1 | 8/2003 | Shadduck |
| 2003/0204258 A1 | 10/2003 | Graham et al. |
| 2003/0216763 A1 | 11/2003 | Patel |
| 2004/0019379 A1 | 1/2004 | Glick et al. |
| 2004/0056371 A1 | 3/2004 | Liao et al. |
| 2004/0068317 A1 | 4/2004 | Knight |
| 2004/0106929 A1 | 6/2004 | Masket |
| 2005/0027355 A1 | 2/2005 | Murakami et al. |
| 2005/0046794 A1 | 3/2005 | Silvestrini et al. |
| 2005/0090895 A1 | 4/2005 | Peyman |
| 2005/0124983 A1 | 6/2005 | Frey et al. |
| 2005/0137703 A1 | 6/2005 | Chen |
| 2005/0143751 A1 | 6/2005 | Makker et al. |
| 2005/0182488 A1 | 8/2005 | Peyman |
| 2005/0187621 A1 | 8/2005 | Brady |
| 2005/0288784 A1 | 12/2005 | Peyman |
| 2006/0064077 A1 | 3/2006 | Peyman |
| 2006/0079959 A1 | 4/2006 | Christie et al. |
| 2006/0113054 A1 | 6/2006 | Silvestrini |
| 2006/0184243 A1 | 8/2006 | Yilmaz |
| 2006/0232665 A1 | 10/2006 | Schowengerdt et al. |
| 2006/0235428 A1 | 10/2006 | Silvestrini |
| 2006/0235514 A1 | 10/2006 | Silvestrini |
| 2006/0241751 A1 | 10/2006 | Marmo et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |

(56) References Cited

U.S. PATENT DOCUMENTS

| | | |
|---|---|---|
| 2007/0032866 A1 | 2/2007 | Portney |
| 2007/0092592 A1 | 4/2007 | Chiang |
| 2007/0129797 A1 | 6/2007 | Lang et al. |
| 2007/0225691 A1 | 9/2007 | Silvestrini et al. |
| 2008/0033546 A1 | 2/2008 | Liang |
| 2008/0077238 A1 | 3/2008 | Deacon et al. |
| 2008/0100921 A1 | 5/2008 | Nishikawa |
| 2008/0151183 A1 | 6/2008 | Altmann |
| 2008/0208335 A1 | 8/2008 | Blum et al. |
| 2008/0212030 A1 | 9/2008 | Bentley et al. |
| 2008/0220214 A1* | 9/2008 | Uozu ................. B26F 1/18  428/155 |
| 2008/0221674 A1 | 9/2008 | Blum et al. |
| 2008/0255663 A1 | 10/2008 | Akpek et al. |
| 2008/0269884 A1 | 10/2008 | Vannoy |
| 2008/0306587 A1 | 12/2008 | Your |
| 2009/0012505 A1 | 1/2009 | Chernyak |
| 2009/0021692 A1 | 1/2009 | Miller et al. |
| 2009/0287306 A1 | 1/2009 | Smith et al. |
| 2009/0059168 A1 | 3/2009 | Miller et al. |
| 2009/0069817 A1 | 3/2009 | Peyman |
| 2009/0171458 A1 | 7/2009 | Kellan et al. |
| 2009/0204207 A1 | 8/2009 | Blum et al. |
| 2009/0222086 A1 | 9/2009 | Lui et al. |
| 2009/0234448 A1 | 9/2009 | Weeber et al. |
| 2009/0306773 A1 | 12/2009 | Silvestrini et al. |
| 2010/0082100 A1 | 4/2010 | Mikawa |
| 2010/0127412 A1 | 5/2010 | Lake |
| 2010/0149618 A1 | 6/2010 | Sprague |
| 2010/0312336 A1 | 12/2010 | Hong et al. |
| 2011/0037184 A1 | 2/2011 | Shoji et al. |
| 2011/0040376 A1 | 2/2011 | Christie et al. |
| 2011/0125261 A1 | 5/2011 | Portney |
| 2011/0166652 A1 | 7/2011 | Bogaert et al. |
| 2011/0172675 A1 | 7/2011 | Danta et al. |
| 2011/0251685 A1 | 10/2011 | Chu |
| 2012/0109294 A1 | 5/2012 | Olson |
| 2012/0143325 A1 | 6/2012 | Christie et al. |
| 2012/0203239 A1 | 8/2012 | Vukich et al. |
| 2012/0245683 A1 | 9/2012 | Christie et al. |
| 2012/0310338 A1 | 12/2012 | Christie et al. |
| 2013/0053953 A1 | 2/2013 | Silvestrini |
| 2013/0131795 A1 | 5/2013 | Miller et al. |
| 2013/0268071 A1 | 10/2013 | Vilupuru et al. |
| 2014/0131905 A1 | 5/2014 | Webb |
| 2014/0264981 A1 | 9/2014 | Reboul et al. |
| 2014/0277432 A1 | 9/2014 | Silvestrini |
| 2014/0379078 A1 | 12/2014 | Trindade |
| 2015/0025627 A1 | 1/2015 | Christie et al. |
| 2015/0073549 A1 | 3/2015 | Webb et al. |
| 2015/0183173 A1 | 7/2015 | Linhardt et al. |
| 2015/0366658 A1 | 12/2015 | Christie et al. |
| 2016/0081794 A1 | 3/2016 | Silvestrini |
| 2016/0229134 A1 | 8/2016 | Reboul et al. |
| 2017/0143477 A1 | 5/2017 | Christie et al. |
| 2017/0144392 A1 | 5/2017 | Reboul et al. |
| 2017/0189167 A1 | 7/2017 | Vilupuru et al. |

FOREIGN PATENT DOCUMENTS

| | | |
|---|---|---|
| CN | 101322663 | 12/2008 |
| DE | 4134320 | 4/1992 |
| EP | 0165652 | 12/1985 |
| EP | 0443094 | 8/1991 |
| EP | 1173790 | 1/2002 |
| EP | 1674049 | 6/2006 |
| EP | 1548489 B1 | 8/2006 |
| EP | 2319457 | 5/2011 |
| EP | 2243052 B1 | 9/2011 |
| EP | 2365379 | 9/2011 |
| EP | 2455799 | 5/2012 |
| EP | 2823789 | 1/2015 |
| EP | 2364457 B1 | 8/2015 |
| FR | 2620687 | 3/1989 |
| FR | 2649605 | 1/1991 |
| GB | 1276003 | 6/1972 |
| JP | 62-167343 | 7/1987 |
| JP | 64-002644 | 1/1989 |
| JP | H02-7954 | 1/1990 |
| JP | 04-158859 | 6/1992 |
| JP | 06-509731 | 3/1993 |
| JP | H05-65340 | 9/1993 |
| JP | 06-502782 | 3/1994 |
| JP | H07-067896 | 3/1995 |
| JP | 07-265340 | 10/1995 |
| JP | 08-103457 A | 4/1996 |
| JP | H09-502542 | 3/1997 |
| JP | 11-503657 | 8/1997 |
| JP | 07-178125 | 7/1998 |
| JP | 2000-047145 | 2/2000 |
| JP | 2002-537895 | 11/2002 |
| JP | 2003-502109 | 1/2003 |
| JP | 2004-510199 | 4/2004 |
| JP | 2004-538034 | 12/2004 |
| JP | 2005-533576 | 11/2005 |
| JP | 2007-516794 | 6/2007 |
| JP | 2007-523720 | 8/2007 |
| JP | 2008-506710 | 3/2008 |
| JP | S59-54527 | 5/2008 |
| KR | 10-0335722 | 5/2002 |
| RU | 2138837 | 9/1999 |
| SU | 1380743 A1 | 3/1988 |
| WO | WO 87/05797 | 10/1987 |
| WO | WO 95/03747 | 2/1995 |
| WO | WO 95/08135 | 3/1995 |
| WO | WO 96/35397 | 11/1996 |
| WO | WO 98/48715 | 11/1998 |
| WO | WO 00/025704 | 5/2000 |
| WO | WO 00/038594 | 7/2000 |
| WO | WO 00/51682 | 9/2000 |
| WO | WO 00/52516 | 9/2000 |
| WO | WO 00/70388 | 11/2000 |
| WO | WO 2001/010641 | 2/2001 |
| WO | WO 01/15779 | 3/2001 |
| WO | WO 01/17460 | 3/2001 |
| WO | WO 01/19364 | 3/2001 |
| WO | WO 01/082815 | 11/2001 |
| WO | WO 02/076320 | 10/2002 |
| WO | WO 02/102241 | 12/2002 |
| WO | WO 03/020177 | 3/2003 |
| WO | WO 03/022168 | 3/2003 |
| WO | WO 03/061518 | 7/2003 |
| WO | WO 2004/014969 | 2/2004 |
| WO | WO 2004/034917 | 4/2004 |
| WO | WO 2004/105588 | 12/2004 |
| WO | WO 2004/113959 | 12/2004 |
| WO | WO 2005/082265 | 9/2005 |
| WO | WO 2005/020638 | 2/2006 |
| WO | WO 2006/047534 | 5/2006 |
| WO | WO 2006/060380 | 6/2006 |
| WO | WO 2006/113377 | 10/2006 |
| WO | WO 2006/113411 | 10/2006 |
| WO | WO 2006/113563 | 10/2006 |
| WO | WO 2006/113564 | 10/2006 |
| WO | WO 2007/057734 | 10/2007 |
| WO | WO 2007/133384 | 11/2007 |
| WO | WO 2007/142981 | 12/2007 |
| WO | WO 2008/036671 | 3/2008 |
| WO | WO 2008/102096 | 8/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/059214 | 5/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2012/170066 | 12/2012 |
| WO | WO 2013/019871 | 2/2013 |
| WO | WO 2013/082545 | 6/2013 |
| WO | WO 2013/101793 | 7/2013 |

(56) References Cited

FOREIGN PATENT DOCUMENTS

| WO | WO 2013/112589 | 8/2013 |
|---|---|---|
| WO | WO 2013/123265 | 8/2013 |
| WO | WO 2014/054946 | 4/2014 |
| WO | WO 2014/074610 | 5/2014 |
| WO | WO 2014/158653 | 10/2014 |
| WO | WO 2015/021323 | 2/2015 |
| WO | WO 2015/069927 | 5/2015 |
| WO | WO 2015/073718 | 5/2015 |
| WO | WO 2016/081493 | 5/2016 |
| WO | WO 2017/062316 | 4/2017 |
| WO | WO 2017/091520 | 6/2017 |

OTHER PUBLICATIONS

Guyton A.C., Textbook of Medical Physiology, 7th Edition, W.B. Saunders Company, Jan. 1986: Chapter 58, pp. 700-710.

Lu Xuequan, et al. "Radiation preparation and thermo-response swelling of interpenetrating polymer network hydrogel composed of PNIPAAm and PMMA", Radiation Physics and Chemistry, vol. 57, Mar. 2000, pp. 477-480, XP002473596.

Patel, C.K., et al. "Imaging the macula through a black occlusive intraocular lens". Arch. Ophthalmol. Oct. 2010; 128(10):1374-1376.

Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-513.

Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.

International Search Report and Written Opinion for PCT/US2015/061143 dated Feb. 29, 2016 in 11 pages.

\* cited by examiner

FRACTURABLE MASK FOR TREATING PRESBYOPIA

RELATED APPLICATIONS

This application claims priority benefit under 37 C.F.R. § 119(e) to U.S. Provisional Patent Application No. 62/082,007, filed Nov. 19, 2014. The contents and disclosures of which are incorporated herein by reference in their entirety.

BACKGROUND

Field

This application relates generally to the field of intraocular devices. More particularly, this application is directed to intraocular implants and lenses (IOLs) with an aperture to increase depth of focus (e.g. "masked" intraocular lenses), and methods of making the same.

Description of the Related Art

The human eye functions to provide vision by transmitting and focusing light onto the retina using the cornea and the natural crystalline lens. The quality of the focused image depends on many factors including the size and shape of the eye, and the optical power of the cornea and the lens.

Some people suffer from cataracts in which the crystalline lens undergoes a loss of transparency. In such cases, the natural crystalline lens can be removed and replaced with an artificial intraocular lens (IOL).

SUMMARY

A method is disclosed herein, the method comprising: providing an intraocular lens, the intraocular lens comprising a lens body and a mask with an aperture for improving depth of focus; and creating a plurality of fractures in the mask. The plurality of fractures in the mask can be created by manipulating the intraocular lens, such as while injecting the intraocular lens into an eye.

An intraocular lens is also disclosed herein, the intraocular lens comprising: a lens body; and a mask with an aperture for improving depth of focus, wherein the mask is configured to fracture along a plurality of fracture pathways when the intraocular lens is manipulated.

The mask can include a plurality of fracture management locations that cause the plurality of fractures to be more likely to form along selected fracture pathways. The plurality of fracture management locations can be configured to substantially maintain the position of the mask with respect to the lens body after creating the plurality of fractures as compared to the position of the mask with respect to the lens body before creating a plurality of fractures.

The lens body can comprise lens material, wherein the lens material extends through the plurality of holes. The mask can be embedded in the lens body.

The lens body can comprise a lens material that is elastic and the mask can comprise a mask material that is brittle. The mask material can be one that fractures at an elongation of approximately 5% or less. The lens material can be one that fractures at an elongation of approximately 150% or more. In some embodiments, the mask material comprises a blend of approximately 30% polymethyl methacrylate (PMMA) and 70% polyvinylidene difluoride (PVDF).

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Some vision problems, such as cataracts, can be treated by implantation of an artificial intraocular lens (IOL). However, depending upon the type of IOL that is used, the patient may still suffer from defects in his or her non-distance eyesight (e.g., due to the inability to vary accommodation so as to focus on near objects). One technique for treating such defects is by including a mask within the IOL that increases the patient's depth of focus. The intraocular implants of the embodiments described herein include a mask adapted to provide a small aperture for light to pass through to the retina to increase depth of focus using the pinhole effect. The light rays that pass through the mask aperture within the IOL converge at substantially a single focal point on the retina, while the light rays that would not converge at the single point on the retina are blocked by the mask.

Figure 1A:
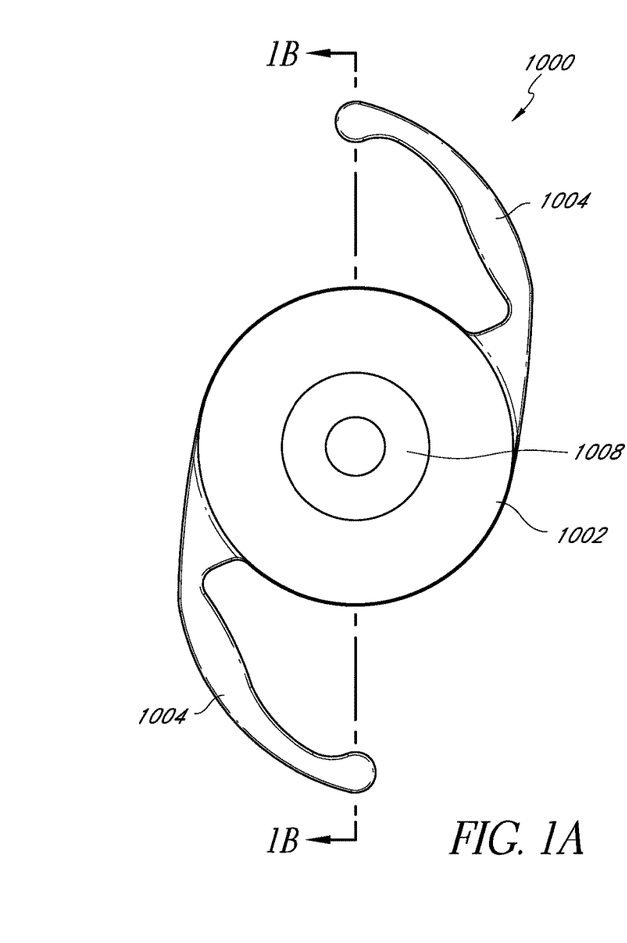
FIG. 1A illustrates a top view of an example embodiment of an intraocular lens having an embedded mask for improving depth of focus.
Figure 1B:
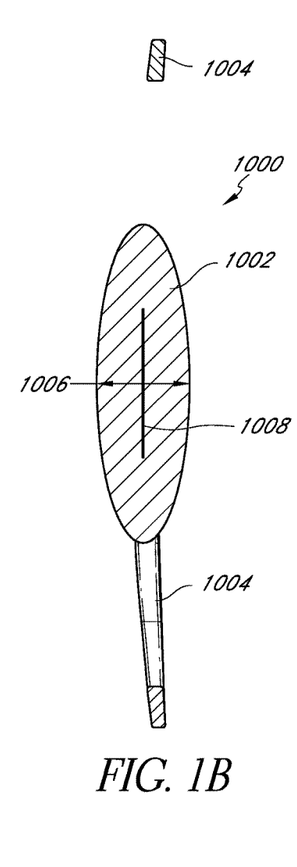
FIG. 1B illustrates a cross-sectional view of the intraocular lens of FIG. 1A taken along line 1B-1B.

FIGS. 1A and 1B illustrate an example embodiment of an intraocular lens having an embedded mask 1008 for increasing depth of focus. The intraocular lens 1000 can include haptics 1004 for positioning the lens within the eye. The cross-sectional thickness of the lens body 1002 is generally dependent on the optical power of the intraocular lens 1000 and the material of the lens body 1002. In particular, the central region of the lens body 1002 is generally the thickest section of the intraocular lens 1000 with a central region cross-sectional thickness 1006.

One method of implanting the IOL 1000 can include inserting the IOL through a small incision in the eye. The IOL 1000 can be inserted into the eye using an injector system. The injector system can include a cartridge tip for housing the IOL 1000. The size of the hole in the cartridge tip through which the IOL 1000 is injected is typically smaller than the size of the IOL. Thus, the IOL 1000 is deformed (e.g., stretched) when passing through the tip during the injection process. The IOL 1000 can be made of a resilient material such that it can revert back to its pre-injection shape after passing through the cartridge tip.

When using this method of implantation, the size of the incision is generally dependent on the size of the cartridge tip. Typically, smaller surgical incisions are associated with better surgical outcomes. However, injecting the IOL 1000 through a smaller hole places more strain on the IOL as it is deformed to pass through the injector.

The size of the cartridge tip and incision can be limited by the material properties of the lens body. This problem can be further complicated by the embedded mask 1008 within the IOL 1000. For example, as the IOL 1000 is pushed through the cartridge tip, the extrusion forces can not only stretch or otherwise deform the IOL but also the embedded mask 1008. In addition, the location of the embedded mask 1008 within the IOL 1000 can be displaced (e.g., the embedded mask can become transversely de-centered and/or longitudinally biased to either side of the desired longitudinal depth of the embedded mask within the IOL).

The mask 1008 and the lens body 1002 may typically be manufactured from dissimilar materials. For example, the mask material and the lens body material may have differences in mechanical properties such as tensile strength (yield strength and/or ultimate strength) and/or elongation under a load. These differences in mechanical properties between the lens body material and the mask material create challenges for the combined IOL 1000 in relation to survival of lens folding and extrusion events that occur during the normal process of lens insertion. After releasing the IOL 1000 from the cartridge tip, it is desirable that the IOL 1000 and the embedded mask 1008 achieve a target post-injection optical performance specification (e.g., optical power, presbyopia correction, etc.). For example, it may be desirable for the post-injection optical performance to substantially match the pre-injection optical performance. However, owing to the differing mechanical properties of the mask material and the lens body material, an IOL constructed with an embedded mask 1008 may be prone to demonstrating relatively poorer optical restoration performance in the post-injection condition.

One solution to the problem of needing to inject the IOL 1000 through a relatively small hole without reducing the optical performance of the IOL, is to provide that both the lens body 1002 and the embedded mask 1008 have similar material properties (e.g., elasticity) that allow them to both spring back to their pre-injection shapes, and, in the case of the embedded mask, its pre-injection location within the IOL. This solution is discussed in U.S. patent application Ser. No. 14/454,585, entitled "INTRAOCULAR LENS WITH ELASTIC MASK," the entirety of which is incorporated by reference herein in its entirety. The following disclosure describes another approach to solving this problem which may be more readily applied to an IOL 1000 where the lens body 1002 and the mask 1008 are made of relatively dissimilar materials.

Embodiments described herein mitigate the difficulties associated with maintaining pre-injection and post-injection optical performance consistency for an IOL 1000 which has a lens body 1002 and an embedded mask 1008 constructed from dissimilar materials. According to some embodiments, the mask 1008 is designed to fracture in a managed way during the lens folding and/or lens injection events. The mask 1008 can be designed with, for example, brittleness and low fracturing forces, while the lens body 1002 can be designed with greater elasticity and relatively longer elongation properties. After the mask 1008 has fractured, the resiliency of the lens body 1002 can relatively freely restore the mask 1008 to its pre-injection shape and/or location upon relaxation. Thus, upon relaxation of the lens body 1002 after injection, the optical performance characteristics of the lens body 1002 in combination with the mask 1008 can be restored.

Provided below are examples of IOLs with embedded masks that are designed to overcome the issues described above. In some implementations, the IOLs (e.g., 1000) with embedded masks (e.g., 1008) that are described herein include substantially the same optical characteristics pre-injection and post-injection.

Masks

Figure 2A:
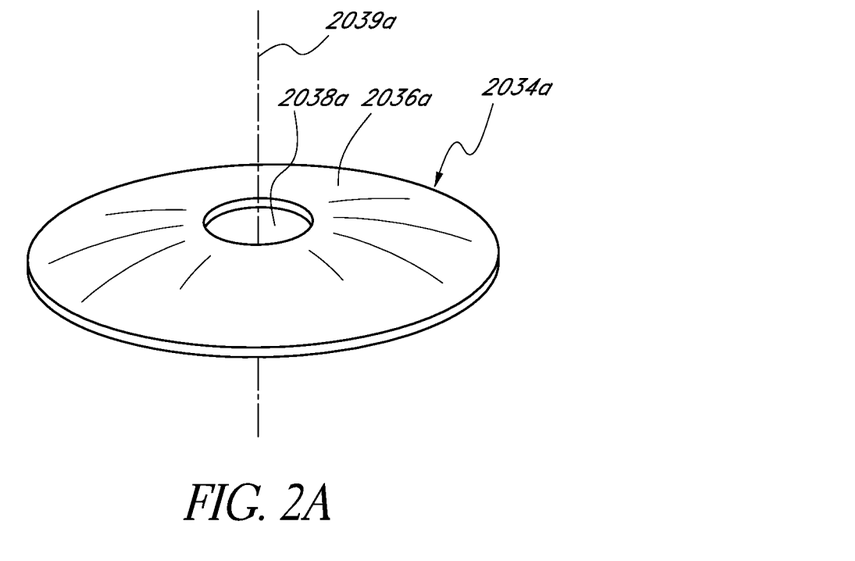
FIG. 2A is a perspective view of one embodiment of a mask configured to increase depth of focus.
Figure 2B:
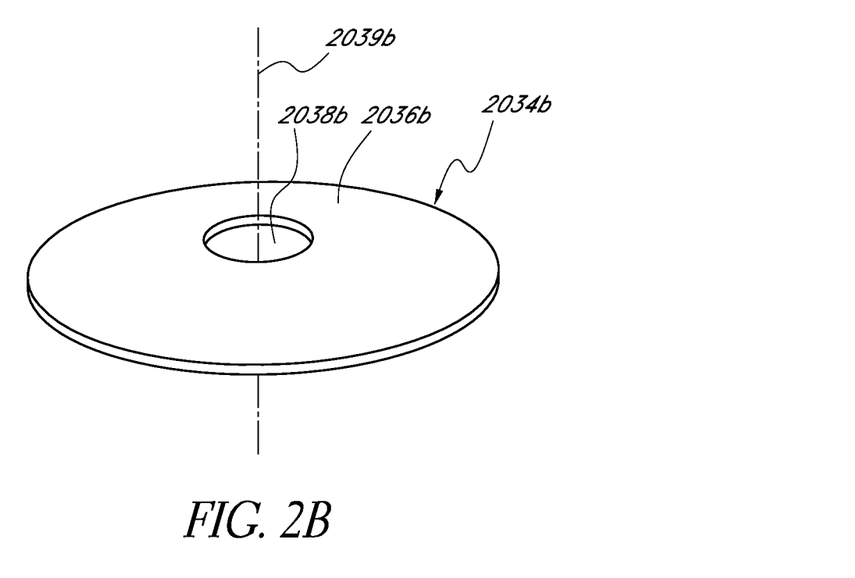
FIG. 2B is a perspective view of an embodiment of a substantially flat mask configured to increase depth of focus.

FIG. 2A illustrates one embodiment of a mask 2034a. The mask 2034a can include an annular region 2036a surrounding an aperture 2038a substantially centrally located on the mask 2034a. The aperture 2038a can be generally located around a central axis 2039a, referred to herein as the optical axis of the mask 2034a. The aperture 2038a can be in the shape of a circle. FIG. 2B illustrates another embodiment of a mask 2034b similar to the mask 2034a illustrated in FIG. 2A. The annular region 2036a of the mask 2034a of FIG. 2A has a curvature from the outer periphery to the inner periphery of the annular region 2036a, while the annular region 2036b of the mask 2034b of FIG. 2B can be substantially flat (as shown in FIG. 1B). Although the examples provided herein are generally discussed in connection with the mask 2034b, any of the examples can include the mask 2034a. In addition, a variety of variations of masks that can be positioned on or within the implant body are discussed herein, and are also described in U.S. Patent Publication No. 2012/0143325, filed Feb. 10, 2012, which is incorporated by reference herein in its entirety. Any of the teachings of this prior publication can also be applied to the devices and methods in the present disclosure.

The mask 2034b can have dimensions adapted to function with the implant body to improve a patient's vision. The mask 2034b can be symmetrical, e.g., symmetrical about a mask axis 2039b. In some embodiments, the outer periphery of the mask 2034b can be circular. The mask 2034b in general can have an outer diameter of at least about 3 mm and/or less than about 6 mm. In some embodiments, the mask 2034b can be circular and can include a diameter of at least about 3 mm and/or less than or equal to about 4 mm. In some embodiments, the mask 2034b can be circular and can include a diameter of about 3.2 mm.

In some embodiments, the aperture 2038b can be substantially circular and can be substantially centered in the mask 2034b. The size of the aperture 2038b can be any size that is effective to increase the depth of focus of an eye of a patient with presbyopia. In particular, the size of the aperture 2038b can be dependent on the location of the mask within the eye (e.g., distance from the retina). In some embodiments, the aperture 2038b can have a diameter of at least about 0.85 mm and/or less than or equal to about 2.2 mm. In certain embodiments, the diameter of the aperture 2038b is less than or equal to about 2 mm. In some embodiments, the diameter of the aperture 2038b is at least about 1.1 mm and/or less than or equal to about 1.6 mm. In some embodiments, the diameter of the aperture 2038b is at least about 1.3 mm and/or less than or equal to about 1.4 mm.

The aperture 2038b can transmit substantially all incident light along the mask axis 2039b. The annular region 2036b can substantially prevent transmission of incident light thereon. The aperture 2038b can be a through-hole in the annular region 2036b or a substantially light transmissive (e.g., transparent) portion thereof. The aperture 2038b of the mask 2034b can be generally defined within the outer periphery of the mask 2034b.

The annular region 2036b can at least partially prevent transmission of visible light through the mask 2034b. For example, in some embodiments, the annular region 2036b can prevent transmission of substantially all or at least a portion of the spectrum of the incident visible light. In some embodiments, the annular region 2036b can prevent transmission of substantially all visible light, e.g., radiant energy in the electromagnetic spectrum that is visible to the human eye. The annular region 2036b can substantially prevent transmission of radiant energy outside the range visible to humans in some embodiments.

Preventing transmission of light through the annular region 2036b can decrease the amount of light that reaches the retina and the fovea that would not converge at the retina and fovea to form a sharp image. As discussed above, the size of the aperture 2038b is such that the light transmitted therethrough generally converges at the retina or fovea. Accordingly, a much sharper image can be presented to the retina than would otherwise be the case without the mask 2034b.

In some embodiments, the annular region 2036b can prevent transmission of at least about 90 percent of incident light. In some embodiments, the annular region 2036b can prevent transmission of at least about 92 percent, at least about 95 percent, or at least about 98 percent of all incident light. The annular region 2036b of the mask 2034b can be substantially opaque to prevent the transmission of light.

In some embodiments, the annular region 2036b can transmit no more than about 5% of incident visible light. In some embodiments, the annular region 2036b can transmit no more than about 3 percent of incident visible light. In some embodiments, the annular region 2036b can transmit no more than about 2 percent of incident visible light. In some embodiments, at least a portion of the annular region 2036b can be opaque to more than 99 percent of the light incident thereon.

As discussed above, the annular region 2036b can prevent at least partial transmission of light without absorbing the incident light. For example, the mask 2034b can be reflective or can interact with the light in a more complex manner, as discussed in U.S. Pat. No. 6,554,424, issued Apr. 29, 2003, which is hereby incorporated by reference in its entirety.

The annular region 2036b can be at least partially opaque or can be completely opaque. The degree of opacity of the annular region 2036b can prevent at least some or substantially all light from being transmitted through the mask 2034b. Opacity of the annular region 2036b can be achieved in any of several different ways. For example, the material used to make mask 2034b can be naturally opaque. As another example, the material used to make the mask 2034b can be substantially clear, but treated with a dye or other pigmentation agent to render region 2036b substantially or completely opaque. In certain embodiments, the mask can include carbon black. In yet another example, the surface of the mask 2034b can be treated physically or chemically (such as by etching) to alter the refractive and transmissive properties of the mask 2034b and make it less transmissive to light.

In some embodiments, a photochromic material can be used as the mask or in addition to mask. Under bright light conditions, the photochromic material can darken thereby creating a mask and enhancing near vision. Under dim light conditions, the photochromic material can lighten, which allows more light to pass through to the retina. In certain embodiments, under dim light conditions, the photochromic material lightens to expose an optic of the intraocular implant. Further photochromic material details are disclosed in U.S. Patent Publication No. 2013/0268071, filed Nov. 30, 2012, which is hereby incorporated by reference in its entirety.

The mask can transition between different degrees of opacity. For example, at least a portion of the mask can transition between at least a first degree of opacity and a second degree of opacity. Further details are disclosed in U.S. application Ser. No. 13/802,340, filed Mar. 13, 2013, which is hereby incorporated by reference in its entirety.

In some embodiments, the opacity of the mask can also vary in different regions of the mask. For example, the opacity of the outer edge and/or the inner edge of the mask can be less than the central region of the mask. The opacity in different regions can transition abruptly or have a gradient transition. Additional examples of opacity transitions can be found in U.S. Pat. Nos. 5,662,706, 5,905,561, 5,965,330, and 8,858,624, all of which are hereby incorporated by reference in their entirety.

Figure 3:
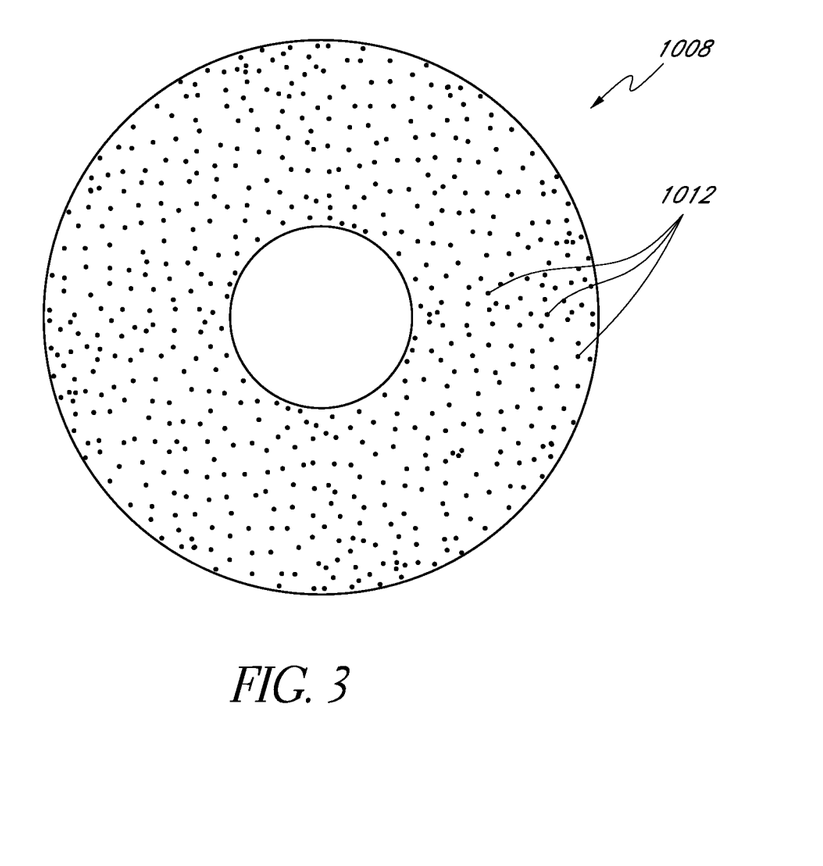
FIG. 3 is a top view of an example embodiment of a fracturable mask configured to increase depth of focus.

FIG. 3 is a top view of an example embodiment of a fracturable mask 1008 configured to increase depth of focus. As illustrated in FIG. 1, the fracturable mask 1008 can be embedded within a lens body 1002 of an intraocular lens 1000. The fracturable mask 1008 can be designed to intentionally fracture along a plurality of fracture pathways when the intraocular lens 1000 is manipulated. For example, a plurality of fractures can be intentionally formed in the fracturable mask 1008 when the intraocular lens 1000 is folded or injected in connection with the implantation process. Alternatively, the fractures can also be formed by manipulating the intraocular lens 1000 during the manufacturing process prior to being shipped to surgical centers.

In some embodiments, the fracturable mask 1008 includes a plurality of fracture management locations 1012. The fracture management locations 1012 cause the mask 1008 to be more likely to fracture along selected fracture pathways. For example, fractures may form along pathways connecting adjacent fracture management locations 1012. Fracture pathways can be selected, for example, by providing fracture management locations 1012 along the desired paths that the fractures are to follow. As discussed further herein, in some embodiments, the fracture management locations are holes that extend through the thickness of the mask 1008 between its anterior and posterior surfaces. In such embodiments, fractures may be more likely to form between each hole and its neighboring hole(s). A series of holes along a desired pathway, or multiple pathways, can create weaknesses that make a fracture, or fractures, more likely to occur along the pathway(s) of holes, similar to how perforations in a sheet of paper help to guide a tear in the sheet of paper. However, in other embodiments, the fracture management locations 1012 can be embodied in other ways, including as weak points and/or impurities in the mask material. Again, the weak points and/or impurities can be arranged so as to make the mask more likely to fracture along a desired pathway or pathways. For example, fractures may be more likely to form between each weak point/impurity and the neighboring weak point(s)/impurity (or impurities). In some embodiments, the fracture management locations 1012 are arranged randomly throughout the fracturable mask 1008 (as shown in FIG. 3). In such embodiments, the fracture pathways can likewise be selected to be arranged randomly.

The fracturable mask 1008 can be designed to fracture relatively easily. This can be done, for example, by forming the fracturable mask 1008 out of a material that is brittle as compared to the lens body material. In some embodiments, the mask material is selected to exhibit elongation at fracture of about 5% or less, or about 3% or less, or about 2% or less. In contrast, the lens material can be selected to exhibit elongation at fracture of about 150% or more. The fracturable mask 1008 can also be made to fracture relatively easily by making the mask relatively thin. In some embodiments, the fracturable mask 1008 is less than approximately 10μ thick, or less than about 6μ thick. In contrast, the lens body 1002 can be at least about 500 times greater in cross-sectional thickness than the mask 1008.

Since the mask 1008 fractures relatively easily, a plurality of fractures can be intentionally formed in the mask while manipulating the resilient lens body 1002. Once the mask has fractured at a plurality of locations, the elastic resiliency of the lens body 1002 can restore the mask 1008 to substantially its same shape and/or location prior to having manipulated the lens body 1002. The fractures are so small, however, that they do not substantially affect the optical performance of the mask 1008.

Materials from which to construct the fracturable mask 1008 can be selected based upon, for example, tensile strength (yield strength and/or ultimate strength) and/or elongation characteristics. Such characteristics can be determined by measuring the stress-strain relationship of a sample made from a selected material.

Figure 4:
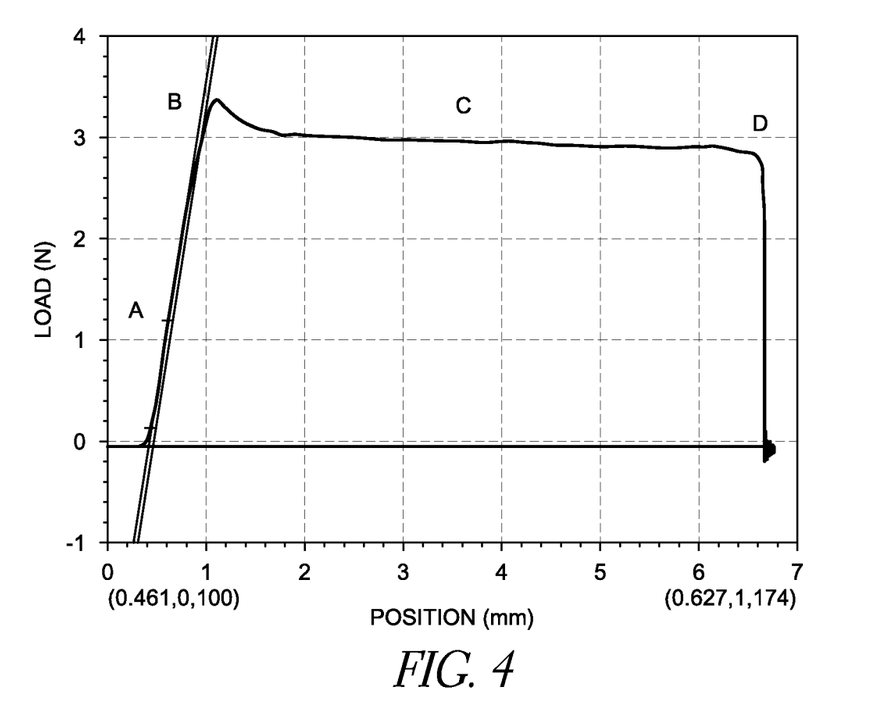
FIG. 4 is a load versus elongation curve which illustrates the tensile properties of a mask made of PVDF.

FIG. 4 is a load versus elongation curve which illustrates the tensile properties of a mask made of polyvinylidene difluoride (PVDF). The curve was measured using a flat material sample having a thickness of about 0.015 mm, a width of about 4.95 mm, and a gauge length of about 22 mm. The tensile load versus elongation curve in FIG. 4 illustrates a region "A" of elastic deformation of the PVDF sample, a yield point "B," a region "C" of plastic deformation, and a break point "D." The PVDF sample was measured as having a yield strength of 40.01 MPa and an ultimate tensile strength of 45.40 MPa. The elongation at yield was 2.273%, as indicated by the 0.2% offset bars on the graph. The extension of the sample at the break point "D" was 6.14 mm, which resulted in a 27.9% elongation at break.

As shown in FIG. 4, the PVDF sample exhibited a relatively large amount of plastic deformation (region "C" of the graph). Plastic deformation is undesirable for the purposes of a fracturable mask 1008 because it can result in the mask not being restored to the same shape it exhibited prior to the applied tensile load (e.g., lens folding and/or injection). Portions of the mask that exhibit plastic deformation but do not break in response to the tensile load do not return to their pre-load state based on the intrinsic properties of the mask material (because the limit of elastic deformation has been exceeded), and further such plastically deformed portions are more resistant to the restorative force of the resilient lens body material as well. Thus, a material that exhibits relatively little plastic deformation and a lower elongation at break would be more desirable for the fracturable mask 1008.

Figure 5:
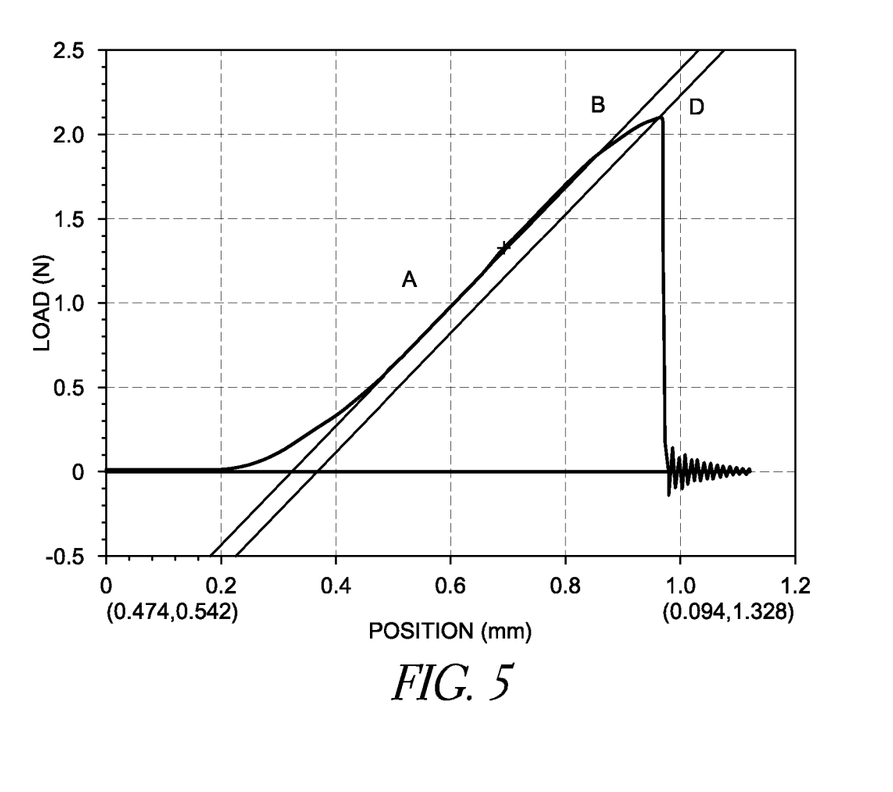
FIG. 5 is a load versus elongation curve which illustrates the tensile properties of a fracturable mask made of a blend of PVDF and PMMA.

FIG. 5 is a load versus elongation curve which illustrates the tensile properties of a fracturable mask 1008 made of a blend of polyvinylidene difluoride (PVDF) and polymethyl methacrylate (PMMA). The sample was approximately 70% PVDF and approximately 30% PMMA. This blend was found to exhibit much more desirable properties for a fracturable mask 1008 than did the pure PVDF sample. The curve in FIG. 5 was measured using a flat material sample having a thickness of about 0.014 mm, a width of about 5.17 mm, and a gauge length of about 22 mm. The tensile load versus elongation curve in FIG. 5 illustrates a region "A" of elastic deformation of the PVDF/PMMA sample, a yield point "B," and a break point "D." Notably, in this sample, the region "C" of plastic deformation is essentially completely missing. The PVDF/PMMA sample was measured as having a yield strength of 29.14 MPa and an ultimate tensile strength of 29.21 MPa. The elongation at yield was 2.818%, as indicated by the 0.2% offset bars on the graph. The extension of the sample at the break point "D" was 0.65 mm, which resulted in only a 3% elongation at break.

As illustrated in FIG. 5, the PVDF/PMMA sample broke essentially immediately after reaching the yield point and without undergoing significant plastic deformation. Thus, the PVDF/PMMA sample was relatively brittle and easily fracturable advantageous properties for the purposes of the fracturable mask 1008. Although a 70%/30% blend of PVDF/PMMA is illustrated, other blends may also be used to the extent that they exhibit elongation at break of less than about 5%. Other materials may also be used if they exhibit similar elongation properties.

As discussed herein, in some embodiments, the fracturable mask 1008 includes a plurality of holes which serve as fracture management locations. In some embodiments, there are at least about 3000 such holes randomly distributed throughout the fracturable mask 1008. Such holes not only serve to cause the mask to fracture in a managed way but they also serve the additional function of mechanically locking the fracturable mask 1008 in place with respect to the lens body 1002. This is true because lens body material can be made to extend through the holes to create a plurality of material bridges that extend between the anterior and posterior surfaces of the fracturable mask 1008. These material bridges remain post-fracture and substantially maintain the pre-fracture position of the fracturable mask 1008 with respect to the lens body 1002 even after fracturing has occurred. Embodiments of fracturable masks with holes serving as the fracture management locations are illustrated in FIGS. 6 and 7.

Figure 6A:
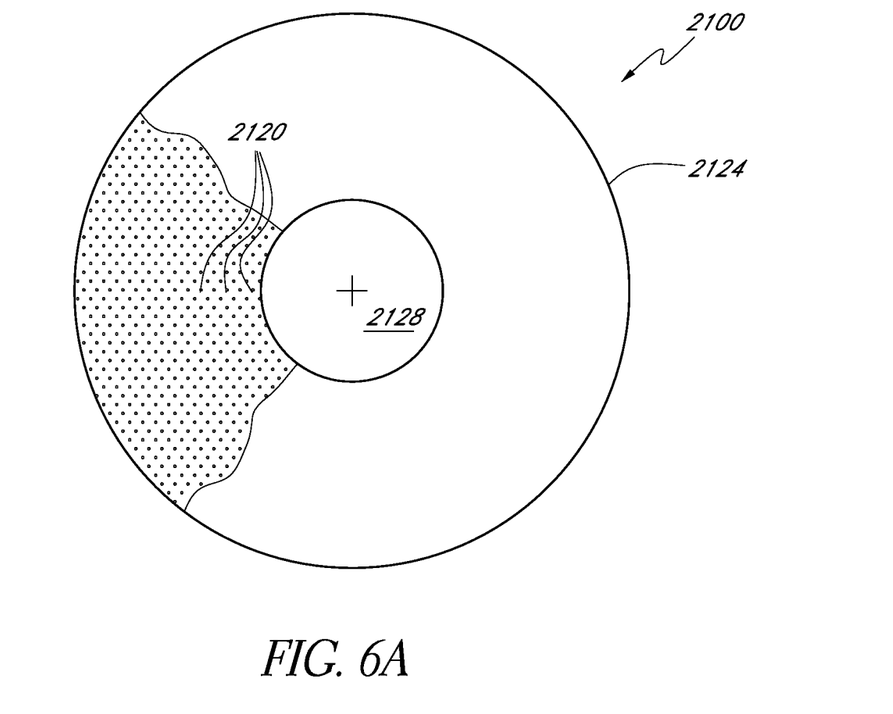
FIG. 6A is a top view of another embodiment of fracturable a mask configured to increase depth of focus.
Figure 6B:
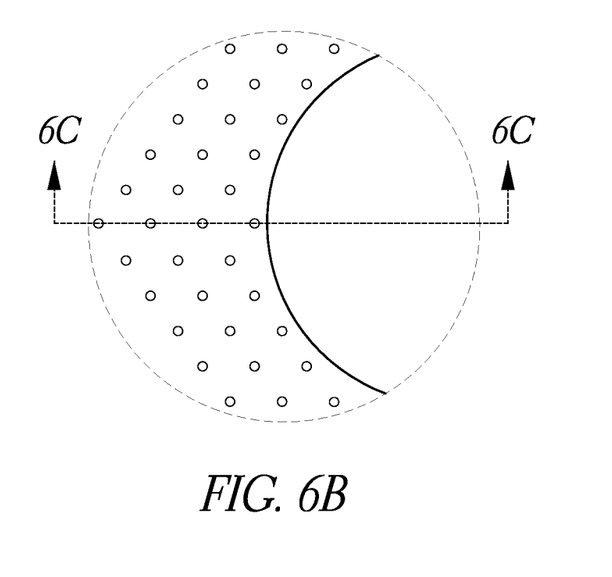
FIG. 6B is an enlarged view of a portion of the view of FIG. 6A.
Figure 6C:
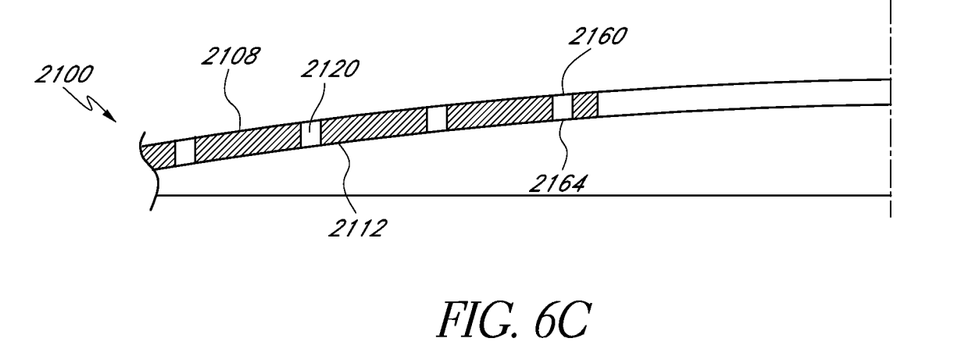
FIG. 6C is a cross-sectional view of the mask of FIG. 6B taken along line 6C-6C.
Figure 7:
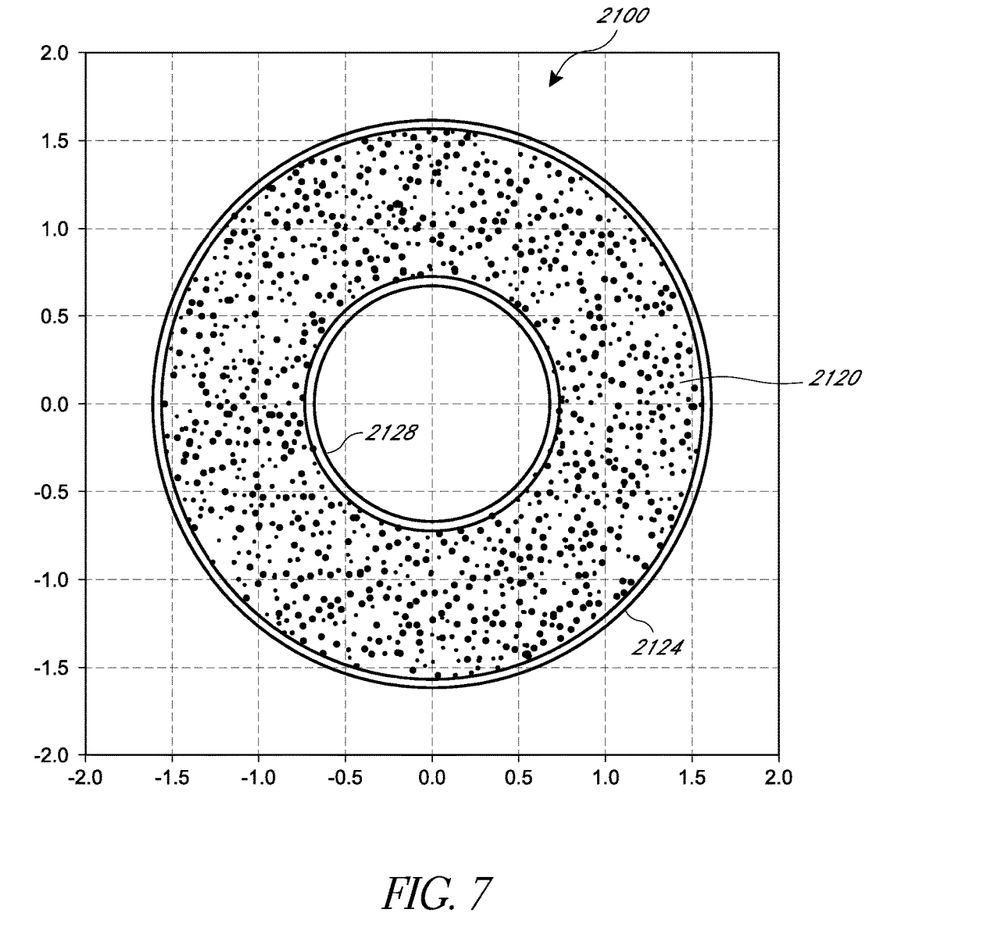
FIG. 7 is a graphical representation of one arrangement of holes that may be formed in a fracturable mask.

FIGS. 6A-6C show another embodiment of a mask 2100 capable of increasing depth of focus of an eye of a patient with presbyopia. The mask 2100 can be flat (as in FIG. 2B) or curved (as in FIG. 2A). The mask 2100 can be similar to the masks hereinbefore described, except as described differently below. The mask 2100 can be made of the materials discussed herein, including those discussed above. In addition, the mask 2100 can be formed by any suitable process. The mask 2100 can be applied to and/or embedded in an IOL.

The mask 2100 can include a plurality of holes 2120. When the mask 2100 is embedded in the lens body, the lens body can extend at least partially through the holes, thereby creating a bond (e.g. material "bridge") between the lens body on either side of the mask. Further disclosure regarding the material "bridge" can be found in U.S. Publication No. 2011/0040376, filed Aug. 13, 2010, which is incorporated by reference herein in its entirety.

The holes 2120 of the mask 2100 shown in FIG. 6A can be located anywhere on the mask 2100. In some embodiments, substantially all of the holes are in one or more regions of a mask. The holes 2120 of FIG. 6A extend at least partially between the anterior surface 2108 and the posterior surface 2112 of the mask 2100. In some embodiments, each of the holes 2120 includes a hole entrance 2160 and a hole exit 2164. The hole entrance 2160 is located adjacent to the anterior surface 2108 of the mask 2100. The hole exit 2164 is located adjacent to the posterior surface 2112 of the mask 2100. In some embodiments, each of the holes 2120 extends the entire distance between the anterior surface 2108 and the posterior surface 2112 of the mask 2100. Further details about possible hole patterns are described in U.S. Patent Publication No. 2012/0143325, filed Feb. 10, 2012, which is incorporated by reference herein in its entirety.

FIG. 7 illustrates a graphical representation of the hole pattern of the mask 2100. In some embodiments, the mask 2100 can include an annular region near the outer periphery 2124 of the mask having no holes. In certain embodiments, there are no holes within 0.1 mm of the outer periphery 2124 of the mask 2100.

The holes in the mask serve at least two purposes: the holes provide some light transmission and, as just discussed with respect to FIGS. 6A-6C, the holes create areas where the material of the implant body can extend through to create a material "bridge" that holds the mask in place. Advantageously, if the mask is in a position between the posterior and anterior surfaces of a lens body, the holes through the mask can help to prevent delamination of the interface between the mask and the lens body. Delamination can occur during manipulation of the intraocular implant such as when the intraocular implant is folded or rolled and placed into a tube to be implanted into the patient. The lens body can extend through the holes, thereby creating a bond (e.g. material "bridge") between the lens body on either side of the mask.

It can be desirable to decrease or minimize the total amount of light that passes through the mask in order to increase or maximize near image contrast. Delamination can be prevented with a relatively small total area of the mask having holes for "bridges". For example, an area of about 3% of the mask can include holes which can balance increasing or maximizing mechanical strength and reducing or minimizing optical effects of the holes. In certain embodiments, the anterior surface of the mask has a mask surface area, and the light transmission structures (e.g., holes) in the mask have a total area on the anterior surface of the mask of about 1% to about 5% of the mask surface area. To limit the visual impact of diffraction of light passing through the holes of the mask, the holes can be made as small as possible. The Airy disc from each hole is larger the smaller the hole size, so the composite diffraction pattern produced by the pattern of holes becomes larger as well. The composite diffraction pattern spreads light over a larger portion of the retina, decreasing the local brightness of diffracted light and making diffraction artifacts less visible to the patient. Diffraction patterns produced by a pattern of holes also tends to have a chromatic component such that the diffraction halo tends to graduate in color radially. Varying the size of the holes produces this effect in multiple scales, which scrambles the color of the halo. This reduces color contrast in the halo, making it less noticeable.

The outer diameter of the outer periphery of the mask can be varied. In certain embodiments, the outer diameter is selected to selectively allow an amount of light to pass to the retina of the eye. The pupil of the eye changes size in different lighting conditions. In low light situations, the pupil of the eye enlarges to let more light into the eye. The outer diameter can be selected so that light does not pass outside the outer periphery of the mask in relatively high light conditions, and so that at least some light can pass outside the outer periphery of the mask in relatively low light conditions. The pupil size of patients often can vary; therefore, the outer diameter of the mask can be selected for a specific patient pupil size. For example, for patients with relatively small pupils, dim light may present more of a vision issue than for patients with larger pupils. For smaller-pupil patients, a mask with more light transmission and/or a smaller outer diameter will increase light reaching the retina and improve vision in dim light situations. Conversely, for larger pupil patients, less light transmission and/or a larger outer diameter mask may improve low-contrast near vision and block more unfocused light. The masked IOLs of the present application give the surgeon flexibility to prescribe the appropriate combination of masked IOL features for particular patients.

In certain embodiments, the center of the aperture of the mask is off-center to the center of the lens body. By having an aperture off-center to the optical center of the lens body, the intraocular lens can be rotated during the implantation procedure so that the optical center of the patient's eye can be aligned with the center of the aperture. The vision of the patient can be improved by aligning the optical center of the patient's eye with the aperture center.

In some embodiments, the mask 2100 can include an annular region near the outer periphery 2124 of the mask having no holes. In certain embodiments, there are no holes within 0.1 mm of the outer periphery 2124 of the mask 2100.

In some embodiments, the mask can include an annular region around the inner periphery of the mask having no holes. In certain embodiments, there are no holes within 0.1 mm of the aperture 2128.

In some embodiments, the holes 2120 each have the same diameter. In certain embodiments, the holes 2120 can include one or more different diameters. In some embodiments, the diameter of any single hole 2120 is at least about 0.01 mm and/or less than or equal to about 0.02 mm. In some embodiments, the diameter of the holes 2120 can vary within 0.001 mm of one or more of the following hole diameters: 0.010 mm, 0.013 mm, 0.016 mm, and/or 0.019 mm. In some embodiments, holes of different diameters are interspersed throughout at least a portion of the mask 2100. In some embodiments, the holes are interspersed at irregular locations throughout at least a portion of the mask 2100.

In certain embodiments, the mask includes holes greater than about 7 microns in diameter (e.g., greater than a cross-sectional area of about 35 $\mu m^2$), and preferably greater than about 10 microns in diameter (e.g., greater than a cross-sectional area of about 75 $\mu m^2$). In certain embodiments, the mask includes holes greater than about 7 microns in diameter (e.g., greater than a cross-sectional area of about 35 $\mu m^2$) and less than about 20 microns in diameter (e.g., less than a cross-sectional area of about 320 $\mu m^2$). In further embodiments, the mask includes holes less than about 50 microns in diameter (e.g., less than a cross-sectional area of about 2000 $\mu m^2$. Holes with diameters less than 7 microns may not be large enough for lens material such as silicone or acrylic to enter and migrate to form a bridge. However, the viscosity of the lens material will determine whether the material will be able to migrate into the hole to form the bridge and a minimum cross-sectional area of the hole may be dependent on the material of the implant body. If the material of the implant body does not migrate into a hole, that hole may create a bubble that could interfere with the visual performance of the implant.

In a certain embodiment, the mask includes randomly or pseudo-randomly placed holes across the mask. The mask can include holes with one of four hole diameters within the parameters provided above. There can be an equal number of holes with each hole diameter. An algorithm can be used to randomly or pseudo-randomly assign the variously sized holes to locations across the mask annulus. The rules for the randomization program can include (1) that there be no "collisions" of the holes (e.g., the holes have no contact with each other), (2) that no holes interfere with the inner and outer peripheral edges of the mask, and (3) that the holes are placed in such a way as to create substantial uniform density across the mask annulus. For example, the rules for the randomization program may include one or more of these rules.

In some embodiments, there are at least about 1000 holes and/or less than or equal to about 2000 holes. In some embodiments, there are at least about 1000 holes and/or less than or equal to about 1100 holes. In some embodiments, the number of holes is within ten holes of about 1040 holes. In some embodiments, there are an equal number of holes of each diameter. In some embodiments, the number of holes having each diameter is different.

In some embodiments, the holes are interspersed at irregular locations throughout at least a portion of the mask 2100. In some embodiments, holes of different diameters are evenly interspersed throughout at least a portion of the mask 2100. For example, the mask 2100 can include a plurality of non-overlapping hole regions. The sum of the surface area of the plurality of non-overlapping hole regions can equal the total surface area of the entire hole region of the mask. In some implementations, each region of the plurality of regions can include a number of holes, each of the holes having a different diameter. In some implementations, the number of holes in each region can equal the number of different hole sizes in the entire hole region. In some implementations, an amount of open area within each hole region can be substantially the same. In some implementations, each hole region can include the same number of holes.

Methods of Use

Any of the IOLs described herein can be implanted using an injection system. The method can include intentionally fracturing the mask embedded in the IOL by, for example, injecting the IOL through a small cartridge tip. The cartridge tip may have an inside diameter of less than or equal to about 2.0 mm, for example, within about 0.2 mm of about 1.5 mm, preferably less than or equal to about 1.5 mm, such as between about 1.5 mm and about 1.25 mm or between about 1.25 mm and about 1.0 mm. The injection system can deliver the IOL through an incision having a chord length of less than or equal to about 2.4 mm. The IOL can be configured to transition between a pre-injection configuration (e.g., rolled up for implantation) and a post-injection configuration (expanded, in-situ shape). The pre-injection configuration can be substantially smaller than the post-injection configuration.

In some implementations, it can be desirable for the IOL to transition between the pre-injection configuration and the post-configuration without substantially changing optical performance. For example, the optical power of the IOL prior to injection can be within about 0.5 diopters, preferably within about 0.3 diopters, or within about 0.2 diopters, or within about 0.1 diopters, of the optical power of the IOL after injection.

Methods of Manufacturing

Various techniques can be used for forming the mask. In some embodiments, the mask can be formed using a mask material alone or in combination with an opacification agent. The mask material can include any of the mask materials described herein, for example, PVDF, silicone, or an acrylic copolymer (e.g., PMMA). In some implementations, the mask material can be combined with an opacification agent, such as carbon black, or any class 3 medical device material.

In some embodiments, the resulting mixture can be used to form a mask film having a thickness equal to the desired mask thickness. Techniques for forming the mask film can include allowing mask material to spread to a desired thickness by gravity or by spinning. Each mask can then be formed from the mask film using a stamp, sieve, die, laser, or other machine. In an alternative technique, the mask material can be formed into a tube (e.g., using an extrusion process), and masks having the desired thickness can be cut from the tube. Further mask materials and methods of making a mask are disclosed in U.S. Pub. No. 2011/0040376, filed Aug. 13, 2010, which is incorporated by reference herein in its entirety.

After forming the mask, the mask can be embedded within or applied to a lens body. For example, the method can include pre-dosing a first lens forming mold portion with a first amount of lens material and positioning the mask on a positioning mold portion. Thereafter, the first lens forming mold portion and the positioning mold portion can be joined together, and the lens material can be at least partially cured. After partially curing the lens material, at least the first lens forming mold portion can be cooled to facilitate the separation of the mold portions without disrupting the position of the mask. Once the mold portions are separated, a second amount of lens material can be added to the first lens forming mold portion and/or a second lens forming mold portion, and the first lens forming mold portion and the second lens forming mold portion can be joined together. In this configuration, the first and the second amounts of lens material can be at least partially cured, for example, using a light cure. Finally, the final curing process can be carried out using thermal curing. In some implementations, depending on the mask and lens materials, the IOL can undergo chemical extraction to remove any impurities. Further details regarding this manufacturing method or alternatives can be found in U.S. patent application Ser. No. 13/830,889 and U.S. Publication No. 2014/0131905, both filed Mar. 14, 2013, which are incorporated by reference herein in their entireties.

Alternatively, the intraocular lens can be manufactured using stereolithography to image the mask within the lens. The method can include providing a first amount of photoreactive lens material. Next, the method can also include forming a first layer of the intraocular lens by curing the first amount of photoreactive lens material to form the desired shape. Thereafter, the method can include providing a second amount of photoreactive lens material over the cured first layer and forming a second layer of the intraocular lens by curing the second amount of photoreactive lens material to form the desired shape. This process can be repeated to additively form the lens. After one or more initial layers of the lens have been formed, a mask can be imaged within the initial layers by activating dyes such as those described in U.S. Publication No. 2013/0268071, filed Nov. 30, 2012, and U.S. Pat. No. 8,604,098, filed Jul. 6, 2011, which are incorporated by reference herein in their entireties, by laser ablation, or by other methods to create opacity, as described in U.S. Publication 2013/0289543, filed Mar. 12, 2013, which is also by incorporated by reference herein in its entirety. Once the mask is in place, the process of providing and curing layers of photoreactive lens material can be continued such that the mask is embedded within the completed lens. The lens can be formed such that the mask can be imaged within the lens in a manner that provides the mask with the same physical properties as the lens, thus allowing the mask to flex with the lens without damage.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although certain embodiments and examples have been described herein, it will be understood by those skilled in the art that many aspects of the methods and IOLs shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A method comprising:
   providing an intraocular lens, the intraocular lens comprising a lens body and a mask with an aperture for improving depth of focus; and
   creating a plurality of fractures in the mask.

2. The method of claim 1, wherein creating the plurality of fractures in the mask is done by manipulating the intraocular lens.

3. The method of claim 2, wherein manipulating the intraocular lens comprises injecting the intraocular lens into an eye.

4. The method of claim 1, wherein the mask comprises a plurality of fracture management locations that cause the plurality of fractures to be more likely to form along selected fracture pathways.

5. The method of claim 4, wherein the selected fracture pathways comprise the fracture management locations.

6. The method of claim 4, wherein the fracture management locations comprise a plurality of holes formed through the mask.

7. The method of claim 4, wherein the plurality of fracture management locations are configured to substantially maintain the position of the mask with respect to the lens body after creating the plurality of fractures as compared to the position of the mask with respect to the lens body before creating a plurality of fractures.

8. The method of claim 7, wherein the plurality of fracture management locations comprise a plurality of holes and the lens body comprises lens material, and wherein the lens material extends through the plurality of holes.

9. The method of claim 1, wherein the mask is embedded in the lens body.

10. The method of claim 1, wherein the lens body comprises a lens material that is elastic and the mask comprises a mask material that is brittle.

11. The method of claim 10, wherein the mask material fractures at an elongation of approximately 5% or less.

12. The method of claim 1, further comprising, after creating the plurality of fractures in the mask, restoring the mask to substantially the same shape as a shape of the mask prior to creating the plurality of fractures.

13. The method of claim 12, wherein an elastic resiliency of the lens body restores the mask to substantially the same shape as the shape of the mask prior to creating the plurality of fractures.

14. The method of claim 1, further comprising, after creating the plurality of fractures in the mask, restoring the mask to substantially the same location relative to the lens body as a location of the mask prior to creating the plurality of fractures.

15. The method of claim 14, wherein an elastic resiliency of the lens body restores the mask to substantially the same location as the location of the mask prior to creating the plurality of fractures.

16. The method of claim 1, wherein creating the plurality of fractures in the mask allows a post-injection optical performance of the intraocular lens to substantially match a pre-injection optical performance of the intraocular lens.

* * * * *